United States Patent
Keller et al.

(10) Patent No.: US 6,589,509 B2
(45) Date of Patent: Jul. 8, 2003

(54) CLEAR, TWO-PHASE, FOAM-FORMING AEROSOL HAIR CARE PRODUCT

(75) Inventors: Walter Keller, Ober-Ramstadt (DE); Karl-Heinz Kischka, Darmstadt (DE)

(73) Assignee: Wella AG, Darmstadt (DE)

( * ) Notice: Subject to any disclaimer, the term of this patent is extended or adjusted under 35 U.S.C. 154(b) by 0 days.

(21) Appl. No.: 09/899,788

(22) Filed: Jul. 5, 2001

(65) Prior Publication Data
US 2002/0031478 A1 Mar. 14, 2002

(30) Foreign Application Priority Data
Jul. 8, 2000 (DE) .......................... 100 33 414

(51) Int. Cl.$^7$ ................................. A61K 7/08
(52) U.S. Cl. ................ 424/47; 424/45; 424/70.12; 424/70.13; 424/70.14; 424/70.15; 424/70.16; 424/70.21; 424/70.27; 424/70.28
(58) Field of Search ............ 424/45, 47, 70.12, 424/70.13, 70.14, 70.15, 70.16, 70.21, 70.27, 70.28

(56) References Cited

U.S. PATENT DOCUMENTS 6,045,779 A * 4/2000 Mueller et al. ............. 132/202
6,117,436 A * 9/2000 Flemming et al. .......... 424/400
6,241,971 B1 * 6/2001 Fox et al. ..................... 424/47
6,328,950 B1 * 12/2001 Franzke et al. ............. 424/401

OTHER PUBLICATIONS

Fatty Acids—Introduction, Rolf Brockmann et al, Ullmann's Encyclopedia of Industrial Chemistry 2002, Wiley–VCH Verlag GMBH, Weinheim, Germany.

Fatty Alcohols—Introduction, Klaus Noweck, Ullmann's Encyclopedia of Industrial Chemistry, 2002, Wiley–VCH Verlag GMBH, Weinheim, Germany.

* cited by examiner

*Primary Examiner*—Jyothsan Venkat
(74) *Attorney, Agent, or Firm*—Michael J. Striker

(57) ABSTRACT

The product for hair treatment includes a transparent pressure-resistant aerosol container and a device for making foam from an effective-ingredient containing composition contained in the aerosol container. The effective-ingredient containing composition contained in the transparent aerosol container has two clearly distinguishable liquid phases with a sharply distinct phase boundary. The two liquid phases consist of a hydrophilic phase and a hydrophobic phase. The hydrophilic phase includes water or a solvent system containing water and a water-soluble organic solvent, at least one cationic or cationically-active hair care ingredient and at least one organic or inorganic salt. The hydrophobic phase contains a water-insoluble, liquefied propellant gas and at least one water-insoluble, hydrophobic, oily or fatty substance dissolved in the liquefied propellant gas.

22 Claims, No Drawings

CLEAR, TWO-PHASE, FOAM-FORMING AEROSOL HAIR CARE PRODUCT

BACKGROUND OF THE INVENTION

The subject matter of the present invention is a product for hair treatment comprising a transparent pressurized container, an effective ingredient containing composition consisting of two clear, liquid phases clearly distinct from each other and a device for forming foam from the composition. The effective-ingredient-containing composition is dispensed from the pressurized container as foam and distributed on the hair. It can be used either as a leave-in-product and remains on the hair or it can be used as a rinse-out product and after a certain acting time it can be removed from the hair.

Hair care compositions, which are dispensed from pressurized containers as foams, are known and are designated as aerosol foams, foam aerosols or as care foams. These products comprise a pressurized container, a foam-generating top or head, an aqueous liquid phase and a liquid propellant gas phase. These products usually require a nontransparent container, for example made from metal or nontransparent plastic, since inhomogeneous, non-cosmetic and unattractively appearing turbid or cloudy masses form streaks at the phase boundary between the liquid propellant gas phase and effective ingredient-containing phase because of the interaction of propellants, effective ingredients, auxiliary ingredients and solvents. Alternatively, or in addition, one or both phases become turbid because of the combination of particular ingredients. However transparent containers are desirable because then it is easy to detect the amount of the composition remaining in the container, i.e. the filling state, whether or not sufficient mixing of the phases has occurred after shaking and, in some cases, whether or not a color of the contents has formed. Generally the transparent products of this kind have greater attractiveness.

SUMMARY OF THE INVENTION

It is an object of the present invention to provide a pressurized transparent hair care product for forming a foam, which is characterized by a distinctive streak-free reversible phase separation between an aqueous effective ingredient-containing phase and a liquid propellant phase, which is observable from the outside after shaking, without impairing the conventional hair care properties of the known conventional foams, or at least without significantly impairing them.

It has been found now that this object is attained in a hair treatment product comprising (A) a transparent pressure-resistant aerosol container,
(B) a device for forming foam from a composition in the container,
(C) an effective ingredient-containing composition in the container comprising two liquid phases (D) and (E), which composition forms a foam when being dispensed from the container (A) by means of the foam-forming device (B) and in which (c1) both liquid phases are transparent and (c2) both liquid phases are separated from each other by a sharp or distinct phase boundary,
wherein (D) one of the liquid phases is hydrophilic and contains water or a solvent system comprising water and a water-soluble organic solvent, wherein (d1) the hydrophilic phase contains at least one cationic or cationically-active hair care ingredient and (d2) the hydrophilic phase contains at least one inorganic salt or non-polymeric organic salt, in which the cation of the salt is a metal ion or an ammonium ion, and
(E) the second liquid phase is hydrophobic and (e1) contains at least one water-insoluble propellant gas present in liquid form under the pressure conditions existing in the aerosol container and (e2) the hydrophobic phase contains at least one water-insoluble hydrophobic substance dissolved in the liquid propellant gas (e1).

The salt (d2) and the hydrophobic substance (e2) of course each alone improve the sharpness of the phase separation, i.e. they both produce a more distinct phase separation. The desired particularly distinct phase separation is however achieved by a synergistic action when the salt (d2) is added to the hydrophilic phase and the hydrophobic substance (e2) is added to the hydrophobic phase (see the comparative tests in example 6).

The cationic or cationically-active hair care substance (d1) is contained in the composition contained in the product according to the invention preferably in an amount of from 0.05 to 10, especially preferably from 0.1 to 5, percent by weight. The salt (d2) is preferably contained in the composition in an amount of from 0.05 to 2, especially preferably from 0.1 to 1.0, percent by weight.

The oily or fatty substance (e2) is preferably present in the composition in an amount of from 0.5 to 10, especially preferably from 1 to 5 percent by weight. The percentages of or amounts of the various ingredients are based on the total amount of the composition present.

The product according to the invention is packaged in a suitable pressure-tight aerosol container and includes a device for forming foam from the composition contained in the container as an additional component. For example, a commercial aerosol foam-forming head can be used as the device for forming foam from the composition. The container is made from a transparent material, through which the consistency, the filling height and the color of the composition are observable. Also because the container is transparent the extent of the mixing or separation of the two liquid phases is observable. The transparent container can be made from glass or transparent pressure-resistant plastic material. The plastic material is preferable on the basis of cost and weight. Polyethylene terephthalate is especially preferred as the plastic material for the transparent container.

Both liquid phases are clear, within the sense of the present invention, when no turbidity or streaking is detected with the naked eye. The phases are distinctly separated from each other within the sense of the present invention when no boundary layer, but only a phase separation line less than 1 mm, preferably less than 0.1 mm, is observable with the naked eye between the phases.

Solvents for the Hydrophilic Phase

The hydrophilic phase contains water either as the sole solvent or in a mixture with alcohol. The alcohol ingredient can comprise especially lower univalent alcohols having one to four carbon atoms, which are commonly employed for cosmetic purposes, such as ethanol and isopropanol, or multivalent alcohols with two to six carbon atoms, such as ethylene glycol, glycerol, propylene glycol, butylene glycol or pentandiol. The water content amounts preferably to 55 to 98% by weight, especially preferably 60 to 95% by weight, and the alcohol content amounts to preferably from 0 to 40, especially preferably 1 to 20, percent by weight, based on the total amount of the composition.

The hydrophilic phase preferably has a pH in a range of from 2 to 7, especially preferably from 4 to 6.5. The pH can be adjusted in the acid range with cosmetically compatible organic or inorganic acids, such as formic acid, tartaric acid, malic acid, maleic acid, fumaric acid, pyrrolidone carboxylic acid, citric acid, lactic acid, sulfuric acid, acetic acid, hydrochloric acid, phosphoric acid, among others.

Cationic Hair Care Ingredients

The cationic or cationically-active ingredients (d1) are substances, which have substantivity for human hair based on cationic or cationizable groups, especially protonated amine groups or quaternary ammonium groups. The cationic or cationically-active hair care ingredients (d1) are preferably selected from the group consisting of cationic polymers, cationic surfactants, cationic silicon compounds, cationic derivatized proteins, cationic derivatized protein hydrolyzates and betaine with at least one cationic or cationically-active group.

Particularly good hair-care action is obtained when at least one cationic polymer is combined with at least one cationic surfactant. The best action was obtained, when, in addition, at least one cationic silicon compound is contained, especially one diquaternary terminated polydimethylsiloxane.

Suitable cationic surfactants contain quaternary ammonium groups. Suitable cationic surfactants especially include those of the general formula (I):

$$N^{(+)}R^1R^2R^3R^4 X^{(-)} \qquad (I),$$

wherein $R^1$, $R^2$, $R^3$ and $R^4$ independently of each other represent aliphatic groups, aromatic groups, alkoxy groups, polyoxyalkylene groups, alkylamido groups, hydroxyalkyl groups, aryl groups or alkaryl groups each with from 1 to 22 carbon atoms, with the proviso that at least one of the groups $R^1$, $R^2$, $R^3$ and $R^4$ has at least eight carbon atoms and wherein $X^{(-)}$ represents an anion, for example a halogen, acetate, phosphate, nitrate or alkyl sulfate, preferably a chloride. The aliphatic groups can also contain cross-linking or other groups, for example additional amino groups, in addition to the carbon and hydrogen atoms.

Particular cationic surfactants, include, for example, alkyldimethylbenzyl chloride or bromide ammonium salts and alkyltrimethylbenzyl chloride or bromide ammonium salts, such as cetyltrimethylammonium chloride or bromide, tetradecyltrimethylammonium chloride or bromide; alkyldimethylhydroxyethylammonium chloride or bromide; dialkyldimethylammonium chloride or bromide, alkylpyridinium salts, such as lauryl pyridinium chloride or cetyl pyridinium chloride; alkylamidoethyltrimethylammonium ether sulfates and compounds with cationic character, such as amine oxides, for example alkylmethylaminoxide or alkylaminoethyldimethylaminoxide. Cetyltrimethylammonium chloride is especially preferred.

The cationic or cationically-active polymers are suitable as hair care or hair-conditioning polymers. Suitable cationic polymers contain preferably quaternary amine groups. The cationic polymers can be homopolymers or copolymers, in which the quaternary nitrogen groups either are located in the polymer chain backbone or preferably as substituents in one or more of the monomers. The ammonium-group-containing monomers can be copolymerized with monomers that do not contain ammonium groups. Suitable cationic monomers include unsaturated radically polymerizable compounds, which have at least one cationic group, especially ammonium-substituted vinyl monomers, for example, trialkylmethacryloxyalkyl ammonium monomers, trialkylacryloxyalkyl ammonium monomers, dialkyldially ammonium monomers and quaternary vinyl ammonium monomers with cyclic, cationic nitrogen-containing groups, such as pyridinium, imidazolium or quaternary pyrrolidones, e.g. alkylvinylimidizolium, alkylvinylpyridinium or alkylvinylpyrrolidone salts. The alkyl groups of these monomers are preferably lower alkyl groups, such as $C_1$- to $C_7$-alkyl groups, especially preferably $C_1$- to $C_3$-alkyl groups.

The monomers containing ammonium groups can be copolymerized with non-cationic monomers. Suitable comonomers include acrylamides, methacrylamides, alkyl- and dialkylacrylamides, alkyl- and dialkylmethacrylamides, alkylacrylates, alkylmethacrylates, vinyl caprolactones, vinyl caprolactams, vinylpyrrolidones, vinyl esters, such as vinyl acetate, vinyl alcohol, propylene glycol and ethylene glycol, in which the alkyl groups preferably have one to seven carbon atoms, especially one to three carbon atoms.

Suitable polymers with quaternary amine groups are, for example, the polymers having the trade name, Polyquaternium, in the CTFA Cosmetic Ingredient Dictionary, such as methylvinylimidazolium chloride/vinyl pyrrolidone copolymer (polyquaternium-16) or quaternized vinyl pyrrolidone/dimethylaminoethylmethacrylate copolymer (polyquaternium-11) and quaternary silicone polymers or- oligomers, such as silicone polymers with quaternary terminal groups (quaternium-80).

For example, vinyl pyrrolidone/dimethylaminoethyl methacrylate methosulfate copolymers, sold under the trademark Gafquat® 755 N and Gafquat® 734 of GAF Co., USA, are suitable as a cationic polymer in the composition according to the invention. The Gafquat® 734 is especially preferred. Other cationic polymers which are suitable include, for example, the copolymer of polyvinyl pyrrolidone and imidazolimine methochloride sold under the trade name LUVIQUAT® HM 550 by BASF, Germany; the terpolymer of dimethyldiallylammonium chloride, sodium acrylate and acrylamide sold by Calgon, USA under the trade name Merquat® Plus 3300; the terpolymer of vinyl pyrrolidone, dimethylaminoethylmethacrylate and vinyl caprolactam sold under the trademark Gaffix® VC 713 of ISP, USA; the vinyl pyrrolidone/methacryl-amidopropyltrimethyl ammonium chloride copolymer sold under the trademark Gafquat® HS 100 and Gafquat® 734 of GAF Co.

Suitable cationic polymers, which are derived from natural polymers, include cationic derivatives of polysaccharides, for example cationic derivatives of cellulose, starches or guar. Chitosan and chitosan derivative compounds are also suitable. Suitable cationic polymers also include cationic polysaccharides having the general formula (II):

$$G\text{---}O\text{---}B\text{---}N^+R^5R^6R^7 X^- \qquad (II),$$

G is an anhydroglucose group, for example a starch or cellulose anhydroglucose group;

B is a divalent compound group, for example an alkylene, oxyalkylene, polyoxyalkylene or hydroxyalkylene group;

$R^5$, $R^6$ and $R^7$ are, independently of each other, alkyl, aryl, alkylaryl, arylalkyl, alkoxyalkyl or alkoxyaryl groups with up to 18 carbon atoms respectively, wherein the total number of carbon atoms in the $R^5$, $R^6$ and $R^7$ groups is at maximum 20; X is a common counter ion, which has the same significance as in formula I and is preferably chloride. A suitable cationic cellulose polymer is marketed under the trademark Polymer JR® by Amerchol and has the INCI name, polyquaternium-10. Another suitable cationic cellulose compound has the INCI name, polyquaternium-24 and is marketed under the trademark Polymer LM-® by Amerchol. A suitable guar derivative compound is marketed under the trademark Jaguar® R and has the INCI name Guar hydroxypropyltrimonium chloride.

Chitosan, chitosan salts and chitosan derivative compounds are especially preferred as the cationic-active ingredients. Completely or partially deacetylated chitins are used as the chitosan or chitosan derivatives in the compositions according to the invention. Chitin contained in the shell residues from crustaceans is an economical and natural raw material available in large quantities, which is used for making chitosan. The molecular weight of the chitosans varies over a wide range, for example from 20,000 to 5,000,000 g/mol. Low molecular weight chitosans with a molecular weight of from 30,000 to 70,000 g/mol are especially suitable. Preferably the molecular weight however can be over 100,000 g/mol, especially from 200,000 to 700,000 g/mol. The deacetylation degree amounts to preferably from 10 to 99%, especially preferably form 60 to 99%.

A suitable chitosan is, for example, marketed under the trademark Flonac® by the Kyowa Oil & Fat Firm, Japan. It has a molecular weight of 300,000 to 700,000 g/mol and is 70 to 80% deacetylated. A preferred chitosan salt is chitosan pyrrolidone carboxylate, which is marketed for example under the trademark Kytamer® PC of the Amerchol firm, U.S.A. The chitosan contained in it has a molecular weight of about 200,000 to 300,000 g/mol and is deacetylated from 70 to 85%. Quaternarized, alkylated or hydroxyalkylated chitosan derivative compounds, such as hydroxyethylchitosan, hydroxypropylchitosan or hydroxybutyl chitosan, are especially suitable.

The chitosans or chitosan derivative compounds are preferably present in neutralized or partially neutralized form. The neutralization degree for the chitosan or the chitosan derivative compounds is preferably at least 50%, especially preferably between 70 and 100%, based on the number of free base groups. In principle all cosmetically compatible inorganic or organic acids can be used as neutralizing agents. These suitable inorganic or organic acids include formic acid, malic acid, lactic acid, pyrrolidone carboxylic acid, hydrochloric acid, among others, of which the pyrrolidone carboxylic acid and the lactic acid are especially preferred.

Those polymers are preferred, which have a sufficient solubility in water or in water/alcohol mixtures, in order to be present in completely dissolved form in the hydrophilic phase according to the invention. The cationic charge density amounts to preferably from 1 to 7 meq/g.

Suitable cation-active silicone compounds preferably have either at least one amino group or at least one ammonium group. Suitable silicone polymers with amino groups are known under the INCI name amodimethicones. These compounds are polydimethylsiloxanes with aminoalkyl groups. The aminoalkyl groups can be terminal groups or side-chain groups. Suitable amino silicones include those of the general formula (III):

   (III), wherein

R$^8$, R$^9$, R$^{14}$ and R$^{15}$ are, independently of each other, the same or different and represent hydrogen, an alkyl group having one to ten carbon atoms, a phenyl group, a hydroxy group, an acetoxy group or an alkoxy group having one to ten carbon atoms; preferably represent an alkyl group having one to four carbon atoms, especially preferably represent a methyl group;

R$^{10}$ and R$^{16}$ are, independently of each other, the same or different and represent hydrogen, hydroxy, phenyl, acetoxy, an alkyl group having one to ten carbon atoms, a phenyl group, an alkoxy group having one to ten carbon atoms or —(CH$_2$)—NH$_2$ with a=1 to 6; preferably represent an alkyl group having one to four carbon atoms, especially preferably represent a methyl group;

wherein R$^{11}$, R$^{12}$ and R$^{13}$ are, independently of each other, the same or different and represent hydrogen, an unsubstituted hydrocarbon group containing from one to twenty carbon atoms, a substituted hydrocarbon group with O and N atom substituents containing from one to twenty carbon atoms; preferably represent an alkyl group containing from one to ten carbon atoms or phenyl; especially preferably an alkyl group having one to four carbon atoms, and most preferably represent a methyl group;

Q represents —A—N—R$^8$R$^9$ or —A—N—R$^{17}$R$^{18}$R$^{19}$, wherein A represents a divalent alkylene compound group having from one to twenty carbon atoms, which may be substituted with O and N atoms as well as OH groups, and R$^{17}$, R$^{18}$ and R$^{19}$, independently of each other, are the same or different and represent hydrogen, a hydrocarbon group having one to twenty two carbon atoms, preferably a phenyl groups or an alkyl group having one to four carbon atoms; particularly preferred groups for Q include —(CH$_2$)$_3$—NH$_2$, —(CH$_2$)$_3$—NHCH$_2$CH$_2$NH$_2$, —(CH$_2$)$_3$OCH$_2$CHOHCH$_2$NH$_2$, and —(CH$_2$)$_3$—N(CH$_2$CH$_2$OH)$_2$, —(CH$_2$)$_3$$^+$ and —(CH$_2$)$_3$OCH$_2$CHOHCH$_2$N$^+$(CH$_3$)$_2$R$^{20}$, wherein R$^{20}$ represents alkyl groups containing from one to twenty two carbon atoms, which can have OH groups;

X represents a number between 1 and 10,000, preferably between 1 and 1,000; and

Y represents a number between 1 and 500, preferably between 1 and 50.

The molecular weight of aminosilicones preferably is between 500 and 100,000. The amine fraction (meq/g) preferably is in a range of from 0.05 to 2.3, especially preferably from 0.1 to 0.5.

Silicon polymers with two terminal quaternary ammonium groups are particularly preferred. These compounds are known by the INCI name Quaternium-80. Polydimethylsiloxanes with two terminal alkylaminogroups are especially preferred. Suitable quaternary aminosilicones are those compounds of the general formula (IV):

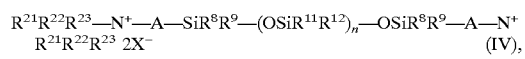   (IV), wherein

A has the same significance as in the above formula (III) and is preferably —(CH$_2$)$_3$OCH$_2$CHOHCH$_2$N$^+$(CH$_3$)$_2$R$^{20}$, wherein R$^{20}$ represents alkyl groups containing from one to twenty two carbon atoms, which can have OH groups; wherein R$^8$, R$^9$, R$^{11}$ and R$^{12}$ have the same significance as in formula (III) above and preferably represent methyl groups;

R$^{21}$, R$^{22}$ and R$^{23}$ represent, independently of each other, an alkyl group having from one to 22 carbon atoms, which can contain hydroxy groups, with the proviso that at least one of the groups contains at least ten carbon atoms and the remaining groups have one to four carbon atoms; n is a number from 10 to 200 and preferably from 10 to 100.

These diquaternary polydimethylsiloxanes are marketed by GOLDSCHMIDT, Germany, under the trademark Abil® Quat 3270, 3272 and 3274.

Additional suitable cationically-active hair care compounds are cationically modified protein derivative compounds or cationically modified protein hydrolyzates, which are known under the INCI names, lauryldimonium hydroxypropyl hydrolyzed wheat protein, lauryldimonium hydroxypropyl hydrolyzed casein, lauryldimonium hydroxypropyl hydrolyzed collagen, lauryldimonium hydroxypropyl hydrolyzed keratin, lauryldimonium hydroxypropyl hydrolyzed silk protein, lauryldimonium hydroxypropyl hydrolyzed soy protein or hydroxypropyltrimonium hydrolyzed wheat protein, hydroxypropyltrimonium hydrolyzed casein, hydroxypropyltrimonium hydrolyzed collagen, hydroxypropyltrimonium hydrolyzed keratin, hydroxypropyltrimonium hydrolyzed rice bran protein, hydroxypropyltrimonium hydrolyzed silk protein, hydroxypropyltrimonium hydrolyzed soy protein, hydroxypropyltrimonium hydrolyzed vegetable protein.

Suitable cationically derivatized protein hydrolyzates are mixed substances, which are obtained for example by reaction of alkaline, acidic or enzymatically hydrolyzed proteins with glycidyltrialkylammonium salts or 3-halo-2-hydroxypropyltrialkylammonium salts. Proteins, which act as raw materials for the protein hydrolyzates, can be of animal or plant origin. Conventional starting materials include keratin, collagen, elastin, soya protein, rice protein, milk protein, wheat protein, silk protein or almond protein. The mixed substances arising by hydrolysis have molecular weights in the range of from about 100 to about 50,000 g/mol. Usually the average molecular weight is in a range between about 500 to 1000 g/mol. Preferably the cationic derivatized protein hydrolyzates have one or two long $C_8$- to $C_{22}$-alkyl chains and correspondingly two or one short $C_1$- to $C_4$-alkyl chains. Compounds, which contain long alkyl chains, are preferred.

Salts

The salts used in the product according to the invention are soluble in water or in the aqueous-alcoholic solvent system of the hydrophilic phase. The cations of the salts used in the invention are metal cations or ammonium cations $NH_4^+$. Univalent, divalent or trivalent metal cations are especially suitable. The cations of the alkali metals and alkaline earth metals, especially sodium, potassium, magnesium and calcium as well as aluminum, are preferred. Chloride, bromide, sulfate, phosphate, nitrate, carbonate and hydrogen carbonate anions are especially suitable as the anions of the salts of the invention. Chloride, sulfate, phosphate and carbonate are particularly preferred. Organic anions formed by deprotonating monomeric organic acids are also suitable, especially deprotonated carboxylic acids having 1 to 10 carbon atoms, in so far as they are water soluble, for example formate, acetate, propionate, lactate, pantothenate, tartrate, malate, pyrrolidone carboxylate or citrate. Sodium chloride, sodium sulfate, magnesium sulfate, especially in the form of the heptahydrate, ammonium chloride, calcium chloride, zinc sulfate, disodium hydrogen phosphate, potassium aluminum sulfate, calcium pantothenate, sodium lactate and calcium acetate, are particularly preferred salts. Also salt mixture with different cations and anions are possible.

Propellant Gas

The propellant gases used in the invention are hydrophobic substances, which are gaseous under normal conditions, i.e. at standard pressure (1013 bar) and room temperature (20° C.). However they are present in liquid form on filling under pressure and are at least partially insoluble in the hydrophilic phase and thus form a second hydrophobic liquid phase. Hydrocarbons having three to five carbon atoms, such as propane, isobutane, n-butane, isopentane or n-pentane, or their mixtures as well as fluorocarbons, such as F 152 (1,1-difluoroethane) or F 134 (tetrafluoroethane), are especially suitable. Mixtures with hydrophilic, partially water-soluble propellant gases, such as dimethyl ether, may also be used, in so far as they not used as the sole propellant, since otherwise the second phase would not form. Pure dimethyl ether also has the disadvantage that it is not compatible with the especially preferred packaging material, transparent plastic, especially polyethylene terephthalate. The container wall can be softened and become unstable, material can be dissolved from the container wall or the ingredients in the effective-ingredient containing solution can diffuse through the wall in the presence of pure dimethyl ether as the sole propellant. Mixtures of propane and butane and mixtures of propane, butane and dimethyl ether are particularly preferred.

The amount of the propellant gas is selected preferably so that after filling the pressure in the aerosol container is at most 2.7 bar at room temperature (20° C.). Typical amounts are from 2 to 30% by weight, preferably 5 to 20% by weight, in relation to the total amount of the composition present.

Hydrophobic Substances

At least one water-insoluble hydrophobic substance (e2) in which the liquid propellant dissolves is an additional essential ingredient of the hydrophobic phase. This hydrophobic substance (e2) is preferably oily or fatty and selected from the group consisting of plant, animal, synthetic or mineral oils, liquid hydrocarbons, especially liquid aliphatic, saturated hydrocarbons, fatty alcohols, fatty alcohol esters, fatty acids, fatty acid esters, especially esters of fatty acids and monoalcohols as well as fatty acid glyceride esters, fatty alcohol ethers and liquid silicone compounds, especially silicone oils.

The following compounds can be used as mineral oils: paraffinum liquidum, paraffinum perliquidum, paraffinum subliquidum, which predominantly represents a mixture of branched and cyclic alkanes. The aliphatic saturated hydrocarbons can be branched or unbranched. Paraffins and isoparaffins, such as isododecane or cyclic hydrocarbons, such as dioctylcyclohexane, etc, are especially suitable.

Suitable plant oils include jojoba oil, olive oil, sunflower oil, avocado oil, etc. For example, neatsfood oil, cod liver oil, mink oil, tallow oil, fish oil, etc, are suitable as animal oils. Suitable fatty alcohols and fatty acids have preferably from 8 to 22 carbon atoms and can be saturated or unsaturated, linear or branched, for example caprylic acid, oleic acid, isostearic acid, etc and/or the corresponding fatty alcohols. Esters of fatty acids with short-chained alcohols ($C_1$- to $C_5$-alcohols), e.g. isopropyl myristate, isopropyl palmitate or isobutyl palmitate, are suitable as the fatty acid esters. Monoglycerides, diglycerides and triglyerides are also suitable fatty acid esters. Esters of fatty acids and fatty alcohols, such as cetyl- or stearyl isononanoate, myristyl myristate, etc, are also suitable. Suitable fatty alcohol esters also includes esters of $C_8$- to $C_{22}$-fatty alcohols with organic acids that are not numbered among the fatty acids, e.g. cetyl lactate, myristyl adipate, etc. Suitable fatty alcohol ethers are built up from two fatty alcohols, which are combined by means of an ether group, e.g. dicapryl ether. Silicone compounds, which can be used, include linear polydimethyl siloxane (dimethicone, hexamethylsiloxane, etc.), cyclic dimethylsiloxane (cyclomethicone), silicone waxes, such as cetyl dimethicone, etc. The hydrophobic substances can be used individually or in a mixture with each other.

An especially reduced load on the treated hair is obtained, when the hydrophobic phase contains at least one hydrophobic, liquid easily volatilized ingredient, which is preferably selected from the volatile silicone compounds and volatile hydrocarbon compounds. The use of ingredients dissolved in the liquid is propellant gas from the aforementioned classes of ingredients, which are easily volatilized at room temperature (20° C.) or when the hair is heated with hot air is recommended in order to prevent an unwanted loaded appearance of the hair. For that reason at least one easily volatilized silicone compound and/or at least one easily volatilized hydrocarbon is provided in an especially preferred embodiment of the invention. The composition is then preferably free of the more-difficult-to-volatilize hydrophobic ingredients or contains them only in an amount of from 3 or less percent by weight. "Easily volatilized ingredients" means, in the sense of this invention, ingredients, which are volatilized from hair strands soaked in these substances without leaving a residue within 20 minutes at a temperature of 100° C. Ingredients are preferred, which have a boiling point under 250° C. at standard pressure. "More-difficult-to-volatilize ingredients" means, within the sense of this invention, ingredients, which are not easily volatized according to the foregoing definition. Suitable easily volatilized ingredients include easily volatilized paraffin compounds, easily volatilized isoparaffin compounds or easily volatilized silicone oils. Branched or unbranched hydrocarbons with 6 to 14 carbon atoms, preferably from 8 to 12 carbon atoms, such as e.g. decane, dodecane, isododecane or additional isomers and linear or cyclic dimethylpolysiloxanes, such as dimethicone or cyclomethicone, are preferred.

Non-volatile hair care ingredients can also be advantageously present in the hydrophobic phase in dissolved form, for example as waxes, e.g. fruit or vegetable waxes, such as apple wax, ilex resin or also lanolin, paraffin wax, petrolatum (Vaseline®) or high viscosity silicone compounds and silicone resins.

Coloring of the Phases

Both liquid phases may be advantageously colored with different colored ingredients. The mixed color produced by shaking prior to application is an optical indicator for sufficient mixing for application. Oil-soluble colored substances soluble in the hydrophobic phase and insoluble in the hydrophilic phase and water-soluble or water/alcohol mixture soluble substances insoluble in the hydrophilic phase are used for this purpose.

Nonionic Polymers

At least one film-forming, nonionic polymer is contained in additional preferred embodiments of the composition according to the invention to improve the hair care properties. The amount used is preferably from 0.05 to 15 percent by weight, especially preferably from 0.5 to 5 percent by weight. Those polymers, which have a sufficient solubility in water or in water/alcohol mixtures, are preferred, so that they are present in the hydrophilic phase in completely dissolved form. The term "film-forming polymer" means, in the sense of the present invention, those polymers, which are in a position to deposit a polymer film on the hair, when present in 0.01 to 5% by weight in an aqueous, alcoholic or aqueous/alcoholic solution.

Suitable synthetic, nonionic, film-forming hair-fixing polymers include homo-or copolymers, which are built up from at least one of the following monomers: vinyl pyrrolidone, vinyl caprolactam, vinyl esters, such as vinyl acetate, vinyl alcohol, acryl amide, methacryl amide, alkyl- and dialkylacrylamides, alkyl- and dialkylmethacrylamides, alkylacrylates, alkylmethacrylates, propylene glycol or ethylene glycol, wherein the alkyl groups of these monomers preferably have from one to seven carbon atoms, especially preferably from one to three carbon atoms.

Homopolymers of vinyl caprolactam, of vinyl pyrrolidone and of N-vinyl-formamide are suitable for example. Additional suitable synthetic film-forming nonionic hair-fixing polymers include, for example, the copolymerizates of vinyl pyrrolidone and vinyl acetate, terpolymers made from vinyl pyrrolidone, vinyl acetate and vinyl propionate, polyacrylamides, polyvinylalcohols and polyethylene glycols/polypropylene glycol copolymers. Suitable natural film-forming polymers include e.g. cellulose derivative compounds, e.g. hydroxyalkyl cellulose compounds, such as hydroxypropyl cellulose compounds with a molecular weight of e.g. 30,000 to 50,000 g/mol. Polyvinyl pyrrolidones and polyvinyl pyrrolidone/vinyl acetate copolymers are especially preferred.

Additional Cosmetic Additive Ingredients

The compositions of the invention can also contain additional cosmetic additive ingredients commonly used in hair treatment compositions, for example preservatives, emulsifiers, solvating agents, perfume oils, fragrance imparting substances, thickeners, pH buffer substances, care ingredients, such as vegetable and plant extracts, protein and silk hydrolyzates, light protective agents, antioxidants, radical trapping agents, anti-flaking agents, luster-imparting substances, vitamins, softeners, combability-improving ingredients, etc.

Preferred Embodiment

An especially preferred embodiment of the active-ingredient-containing composition has the following composition:

(a) from 0.05 to 5.0 percent by weight of at least one water-soluble non-ionic film-forming polymer, (b) from 0.05 to 5.0 percent by weight of at least one water-soluble cationic polymer and/or at least one diquaternary polydimethylsiloxane, (c) from 0.05 to 2.5 percent by weight of at least one water-soluble cationic surfactant, (d) from 0.05 to 2.0 percent by weight of at least one water-soluble inorganic salt and/or a non-polymeric organic salt, in which the cation of the salt is a metal ion or the ammonium ion, (e) from 63.0 to 97.25 percent by weight of water or a water/alcohol mixture, (f) from 0.5 to 5.0 percent by weight of at least one volatile hydrocarbon and/or volatile silicone compound, which are liquids under normal conditions, and (g) from 2.0 to 20.0% by weight of a propellant ingredient, which is propane, butane, mixtures of propane and butane and mixtures of propane or butane with dimethyl ether, wherein the percentages are based on the total amount of the composition.

The product according to the invention is made by first dissolving the ingredients for the hydrophilic phase in the hydrophilic solvent. The ingredients dissolved in the hydrocarbon phase are metered with the propellant gas prior to filling. Finally the propellant gas is filled into the aerosol container and the aerosol contained is tightly closed.

The product can be a rinse product and also a leave-on-product. The cosmetic composition according to the invention is applied to the hair in a sufficient amount to provide the desired hair care effects according to the amount of the hair and the state of the hair (typically about 3 to 10 g) and is distributed on the hair. After an acting time (e.g. 3 to 6 minutes) it can be rinsed out of the hair. Similarly the composition can also be allowed to remain on the hair, which is dried after the application.

The following examples should serve to illustrate the claimed invention in greater detail.

EXAMPLES

Example 1

| | |
|---|---|
| Polyvinylpyrrolidone | 0.2 g |
| Polyquaternium-11 | 0.18 g |
| Cetyltrimethylammonium chloride | 0.25 g |
| Quaternium-80 | 0.45 g |
| $MgSO_4 \cdot 7H_2O$ | 0.2 g |
| Isododecane | 2.5 g |
| Isobutane | 1.4 g |
| Butane | 6.8 g |
| Propane | 1.8 g |
| Water | to 100 g |

This composition is filled into a pressure-resistant container made from transparent polyethylene terephthalate. The container is provided with a foam-forming head and closed.

Example 2

| | |
|---|---|
| PVP/VA Copolymer | 0.35 g |
| Polyquaternium-11 | 0.24 g |
| Cetyltrimethylammonium chloride | 0.12 g |
| Quaternium-80 | 1.10 g |
| $(Na)_2SO_4 \cdot 7H_2O$ | 0.12 g |
| Cyclomethicone | 3.5 g |
| Isobutane | 1.2 g |
| Butane | 5.3 g |
| Propane | 1.5 g |
| Water | to 100 g |

This composition is filled into a pressure-resistant container made from transparent polyethylene terephthalate. The container is provided with a foam-forming head and closed.

Example 3

| | |
|---|---|
| Polyvinylpyrrolidone | 2.5 g |
| Polyquaternium-7 | 2.0 g |
| Cetyltrimethylammonium chloride | 0.55 g |
| Quaternium-80 | 1.60 g |
| Sodium chloride | 0.45 g |
| Calcium acetate | 0.1 g |
| Ethanol | 6.0 g |
| Mineral oil | 2.8 g |

| -continued | |
|---|---|
| Isobutane | 2.1 g |
| Butane | 10.2 g |
| Propane | 2.7 g |
| Water | to 100 g |

This composition is filled into a pressure-resistant container made from transparent polyethylene terephthalate. The container is provided with a foam-forming head and closed.

Example 4

| | |
|---|---|
| Polyvinylpyrrolidone | 0.45 g |
| Polyquaternium-16 | 0.75 g |
| Chitosan | 0.25 g |
| Lactic acid (90%) | 0.20 g |
| Cetyltrimethylammonium chloride | 0.55 g |
| Quaternium-80 | 1.60 g |
| Calcium acetate | 1.0 g |
| Jojoba oil | 1.5 g |
| Octyl dodecanol | 2.0 g |
| Isobutane | 1.4 g |
| Butane | 6.8 g |
| Propane | 1.8 g |
| Water | to 100 g |

This composition is filled into a pressure-resistant container made from transparent polyethylene terephthalate. The container is provided with a foam-forming head and closed.

Example 5

| | |
|---|---|
| PVP/VA Copolymer | 3.8 g |
| Polyquaternium-11 | 0.18 g |
| Polyquaternium-16 | 0.82 g |
| Cetyltrimethylammonium chloride | 0.65 g |
| Quaternium-80 | 2.50 g |
| Calcium pantothenate | 0.65 g |
| Cetyl-stearyl isononanoate | 1.0 g |
| Dicapryl ether | 2.50 g |
| Isostearic acid | 1.50 g |
| Dimethyl ether | 1.0 g |
| Butane | 5.0 g |
| Propane | 4.0 g |
| Water | to 100 g |

This composition is filled into a pressure-resistant container made from transparent polyethylene terephthalate. The container is provided with a foam-forming head and closed.

Example 6

Comparative Tests

Different hydrophobic substances and different salts were added individually and in combination to the following composition having the following general recipe. Whether or not a two-phase composition with a well-defined or sharp phase boundary between the two clear, non-turbid phases was formed, was tested. A sharply defined phase boundary was only observed when a combination of hydrophobic substance and salt was used. The results are summarized in Table I. Amounts listed are based on the total weight of the composition.

| General Recipe: | |
|---|---|
| Polyvinylpyrrolidone (Luviskol ® K80 Powder) | 0.2 g |
| Polyquaternium-11 | 1.0 g |
| Cetyltrimethylammonium chloride | 0.25 g |
| Quaternium-80 | 1.0 g |
| Glyoxylic acid | 0.05 g |
| Ethanol | 5.0 g |
| Water | to 100 g |
| Propane/butane 90/10 at 2.7 bar | |

TABLE I

COMPARATIVE TEST RESULTS

| Hydrophobic Substance | Salt | Sharp Phase Boundary |
|---|---|---|
| 3% isododecane | — | No |
| — | 0.5% $Na_2SO_4$ | No |
| — | 0.1% $Na_2SO_4$ | No |
| 3% isododecane | 0.5% $Na_2SO_4$ | Yes |
| 3% isododecane | 0.1% $Na_2SO_4$ | Yes |
| 3% isododecane | 0.5% $MgSO_4$ | Yes |
| 3% isododecane | 0.5% Ca-acetate | Yes |
| 3% isododecane | 0.5% $NH_4Cl$ | Yes |
| 3% isododecane | 0.5% K-Al-sulfate | Yes |
| 3% isododecane | 0.5% $Na_2SO_4$ | Yes |
| 3% isododecane | 0.5% NaCl | Yes |
| 3% isododecane | 0.5% $CaCl_2$ | Yes |
| 3% isododecane | 0.5% Ca-pantothenate | Yes |
| 3% isododecane | 1% Na-lactate | Yes |
| 3% paraffinum perl. | — | No |
| 3% paraffinum perl. | 0.25% $Na_2SO_4$ | Yes |
| Jojobal oil | — | No |
| Jojoba oil | 0.25% $Na_2SO_4$ | Yes |
| Isopropylmyristate | — | No |
| Isopropylmyristate | 0.5% $Na_2SO_4$ | Yes |
| Cetyl/stearyl-isononanoate | — | No |
| Cetyl/stearyl-isononanoate | 0.25% $Na_2SO_4$ | Yes |
| Cetyl lactate | — | No |
| Cetyl lactate | 0.25% $Na_2SO_4$ | |
| Dicapryl ether | — | No |
| Dicapryl ether | 0.25% $Na_2SO_4$ | Yes |
| Diethylhexyl-Cyclohexane | — | No |
| Diethylhexyl-Cyclohexane | 0.25% $Na_2SO_4$ | Yes |
| Octyldodecanol | — | No |
| Octyldodecanol | 0.25% $Na_2SO_4$ | Yes |
| Cetyl Dimethicone | — | No |
| Cetyl Dimethicone | 0.25% $Na_2SO_4$ | Yes |
| Isostearic acid | — | No |
| Isostearic acid | 0.25% $Na_2SO_4$ | Yes |
| Capryilic Acid | — | No |
| Capryilic Acid | 0.25% $Na_2SO_4$ | Yes |
| Capric Acid | — | No |
| Capric Acid | 0.25% $Na_2SO_4$ | Yes |

The disclosure in German Patent Application 100 33 414.8-41 of Jul. 8, 2000 is incorporated here by reference. This German Patent Application describes the invention described hereinabove and claimed in the claims appended hereinbelow and provides the basis for a claim of priority for the instant invention under 35 U.S.C. 119.

While the invention has been illustrated and described as embodied in clear, two-phase foam-forming aerosol hair care products, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims.

We claim:

1. A product for hair treatment comprising
   a transparent pressure-resistant aerosol container,
   an effective ingredient-containing composition contained in the transparent pressure-resistant aerosol container, said composition comprising two liquid phases, wherein both of said liquid phases are transparent and both of said liquid phases are separated from each other by a sharp or distinct phase boundary, wherein one of the liquid phases is hydrophilic and comprises water or a solvent system, said solvent system including water and a water-soluble organic solvent, wherein the liquid phase that is hydrophilic comprises at least one cationic or cationically-active hair care ingredient and at least one inorganic or non-polymeric organic salt, said at least one inorganic or non-polymeric organic salt comprising a metal cation or an ammonium cation, and another of said liquid phases is hydrophobic and comprises at least one water-insoluble propellant gas present in liquid form under pressure conditions present in the pressure-resistant aerosol container and at least one water-insoluble hydrophobic substance dissolved in the at least one water-insoluble propellant gas present in liquid form; and
   a device for dispensing foam from said transparent pressure-resistant container, said foam being formed from said effective-ingredient-containing composition contained in the pressure-resistant aerosol container.

2. The product as defined in claim 1, wherein said pressure-resistant aerosol container comprises a material and said material consists of transparent pressure-resistant glass or a transparent pressure-resistant plastic.

3. The product as defined in claim 2, wherein said material is polyethylene terephthalate.

4. The product as defined in claim 1, wherein said water-soluble organic solvent is selected from the group consisting of monoalcohols with one to four carbon atoms and polyalcohols with two to six carbon atoms.

5. The product as defined in claim 1, wherein said at least one cationic or cationically-active hair care ingredient has at least one cationic or cationically-active group and is selected from the group consisting of cationic polymers, cationic surfactants, cationic silicone compounds, cationically derivatized proteins, cationically derivatized protein hydrolyzates and betaines.

6. The product as defined in claim 5, wherein said cationic surfactants are surface-active compounds of formula (I):

$$N^{(+)}R^1R^2R^3R^4X^{(-)}$$  (I), wherein
   $R^1$, $R^2$, $R^3$ and $R^4$, independently of each other, are each selected from the group consisting of aliphatic groups with 1 to 22 carbon atoms, alkoxy groups with 1 to 22 carbon atoms, polyoxyalkylene groups with from 1 to 22 carbon atoms, alkylamido groups with 1 to 22 carbon atoms, hydroxyalkyl groups with 1 to 22 carbon atoms, a benzyl group and a pyridinium group; and $X^{(-)}$ represents an anion;
   with the proviso that at least one of said $R^1$, $R^2$, $R^3$ and $R^4$ has at least eight carbon atoms.

7. The product as defined in claim 5, wherein said cationic polymers are selected from the group consisting of vinylimidazolium chloride/vinyl pyrrolidone copolymers, quaternized vinyl pyrrolidone/dimethylaminoethylmethacrylate copolymers, cationically derivatized polysaccharides, chitosan, chitosan salts, quaternized chitosan compounds, alkylated chitosan compounds and hydroxyalkylated chitosan compounds.

8. The product as defined in claim 5, wherein said cationic silicone compounds are diquaternary terminated polydimethylsilioxanes.

9. The product as defined in claim 1, containing from 0.05 to 10 percent by weight, based on a total amount of said composition in said aerosol container, of said at least one cationic or cationically-active hair care ingredient.

10. The product as defined in claim 1, wherein said metal cation is a univalent cation, a divalent cation or a trivalent cation and said at least one inorganic or non-polymeric organic salt includes an anion selected from the group consisting of chloride, sulfate, phosphate and deprotonated organic acids.

11. The product as defined in claim 1, containing from 0.05 to 2 percent by weight, based on a total amount of said composition in said aerosol container, of said at least one inorganic or non-polymeric organic salt.

12. The product as defined in claim 1, wherein said at least one water-insoluble propellant gas is at least one hydrocarbon containing from three to five carbon atoms or a mixture of said at least one hydrocarbon with dimethyl ether.

13. The product as defined in claim 1, wherein said aerosol container contains an amount of said at least one water-insoluble propellant gas so that a pressure in said aerosol container is at most 2.7 bar at 20° C.

14. The product as defined in claim 1, wherein said at least one water-insoluble hydrophobic substance is selected from the group consisting of plant oils, animal oils, mineral oils, synthetic oils, liquid hydrocarbons, fatty alcohols, fatty alcohol esters, fatty acids, fatty acid esters, fatty alcohol ethers and liquid silicone compounds.

15. The product as defined in claim 1, wherein said at least one water-insoluble hydrophobic substance is selected from the group consisting of volatile hydrocarbons and volatile silicone compounds.

16. The product as defined in claim 1, containing from 0.5 to 10 percent by weight, based on a total amount of said composition in said aerosol container, of said at least one water-insoluble hydrophobic substance.

17. The product as defined in claim 1, wherein said effective ingredient-containing composition comprises at least one non-ionic film-forming polymer.

18. The product as defined in claim 17, wherein said at least one non-ionic film-forming polymer is selected from the group consisting of polyvinylpyrrolidone and polyvinylpyrrolidone/vinyl acetate copolymers.

19. The product as defined in claim 17, containing from 0.05 to 5 percent by weight, based on a total amount of said composition in said aerosol container, of said at least one non-ionic film-forming polymer.

20. The product as defined in claim 1, wherein said two liquid phases are differently colored.

21. A product for hair treatment comprising
a transparent pressure-resistant aerosol container;
an effective ingredient-containing composition contained in the transparent pressure-resistant aerosol container; and
a device for dispensing foam from said transparent pressure-resistant container, said foam being formed from said effective-ingredient-containing composition contained in the pressure-resistant aerosol container;
wherein said effective ingredient-containing composition comprises a hydrophilic liquid phase and a hydrophobic liquid phase, said hydrophilic liquid phase and said hydrophobic liquid phase are both clearly visible in the transparent pressure-resistant aerosol container from outside of the container and are separated from each other by a sharp or distinct phase boundary;
wherein said hydrophilic liquid phase comprises water or a solvent system, said solvent system includes water and a water-soluble organic solvent, said hydrophilic liquid phase comprises at least one cationic or cationically-active hair care ingredient and at least one inorganic or non-polymeric organic salt, said at least one inorganic or non-polymeric organic salt comprises a metal cation or an ammonium cation; and
wherein said hydrophobic liquid phase comprises at least one water-insoluble propellant gas present in liquid form under pressure conditions present in the pressure-resistant aerosol container and at least one water-insoluble hydrophobic substance dissolved in said at least one water-insoluble propellant gas present in said liquid form; and
wherein said effective ingredient-containing composition comprises
from 0.05 to 5.0 percent by weight of at least one water-soluble nonionic film-forming polymer,
from 0.05 to 5.0 percent by weight of at least one cationic member selected from the group consisting of water-soluble cationic polymers and diquaternary polydimethylsiloxanes,
from 0.05 to 2.5 percent by weight of at least one water-soluble cationic surfactant,
from 0.05 to 2.0 percent by weight of said at least one inorganic or non-polymeric organic salt;
from 63.0 to 97.25 percent by weight of said water or said solvent system, said solvent system consisting of a water/alcohol mixture,
from 0.5 to 5.0 percent by weight of said at least one water-insoluble hydrophobic substance and said at least one water-insoluble hydrophobic substance is selected from the group consisting of volatile hydrocarbons, volatile silicone compounds, fatty acids, fatty alcohols, fatty alcohol esters, fatty acid esters, fatty alcohol ethers, plant oils, animal oils and mineral oil, and
from 2.0 to 20.0 percent by weight of at least one propellant ingredient and said at least one propellant ingredient is propane, butane, a mixture of said propane and said butane, a mixture of said propane with dimethyl ether or a mixture of said butane with said dimethyl ether.

22. A product for hair treatment comprising
a transparent pressure-resistant aerosol container,
an effective ingredient-containing composition contained in the transparent pressure-resistant aerosol container, said composition comprising two liquid phases, wherein both of said liquid phases are clearly visible in the container and both of said liquid phases are separated from each other by a sharp or distinct phase boundary;
wherein one of the liquid phases is hydrophilic and comprises water or a solvent system, said solvent system including water and a water-soluble organic solvent, and the one of the liquid phases that is hydrophilic comprises at least one cationic or cationically-active hair care ingredient and at least one inorganic or non-polymeric organic salt, said at least one inorganic or non-polymeric organic salt comprising a metal cation or an ammonium cation; and wherein another of said liquid phases is hydrophobic and comprises at least one water-insoluble propellant gas present in liquid form under pressurized conditions present in the transparent pressure-resistant aerosol container and at least one water-insoluble hydrophobic substance dissolved in the at least one water-insoluble propellant gas present in said liquid form; and a device for dispensing foam from said transparent pressure-resistant container, said foam being formed from said effective-ingredient-containing composition contained in the pressure-resistant aerosol container; and wherein said effective ingredient-containing composition contains from 0.05 to 2.0 percent by weight of said at least one inorganic or non-polymeric organic salt, from 0.5 to 5.0 percent by weight of said at least one water-insoluble hydrophobic substance and from 55 to 98 percent by weight water or a mixture of water and alcohol, said alcohol being at least one member selected from the group consisting of univalent alcohols having one to four carbon atoms and multivalent alcohols having from two to six carbon atoms; and wherein said at least one water-insoluble hydrophobic substance is selected from the group consisting of volatile hydrocarbons, volatile silicone compounds, fatty acids, fatty alcohols, fatty alcohol esters, fatty acid esters, fatty alcohol ethers, plant oils, animal oils and mineral oil.

* * * * *